United States Patent [19]
Orr

[11] Patent Number: 5,951,468
[45] Date of Patent: Sep. 14, 1999

[54] METHOD FOR TESTING FOR GASTROESOPHAGEAL REFLUX DISEASE

[76] Inventor: William C. Orr, 5300 N. Independence Ave., Suite 130, Oklahoma City, Okla. 73112

[21] Appl. No.: 08/915,297

[22] Filed: Aug. 20, 1997

Related U.S. Application Data

[60] Provisional application No. 60/024,569, Aug. 26, 1996.

[51] Int. Cl.[6] ........................................................ A61B 5/00
[52] U.S. Cl. ............................................. 600/300; 128/898
[58] Field of Search .................................. 600/300, 301; 128/897, 898

[56] References Cited

U.S. PATENT DOCUMENTS

| | | |
|---|---|---|
| 4,168,703 | 9/1979 | Kenigsberg . |
| 4,503,859 | 3/1985 | Petty et al. . |
| 5,117,827 | 6/1992 | Stuebe et al. . |
| 5,254,591 | 10/1993 | Martin ....................................... 424/156 |
| 5,571,116 | 11/1996 | Bolnos et al. ........................... 606/139 |
| 5,807,452 | 9/1998 | Schwinn ..................................... 156/86 |

*Primary Examiner*—Samuel Gilbert
*Attorney, Agent, or Firm*—Edward G. Fiorito

[57] ABSTRACT

An easy, safe and inexpensive procedure to testing the presence of esophageal acid sensitivity in a patient involves having the patient swallow a controlled quantity of a weak acid solution and a similar-tasting controlled quantity of a neutral solution and recording the reactions or symptoms experienced by the patient during the drinking of each solution. The acid solution only should affect the sensitivity of the esophageal lining in patients with esophageal acid sensitivity, providing heartburn and other related symptoms to include non-cardiac chest pain, but should not have any significant effect on patients without esophageal acid sensitivity. The neutral solution may be altered to simulate the taste of the acid solution and reduce the effect the taste of the solutions may have on the test results.

26 Claims, 1 Drawing Sheet

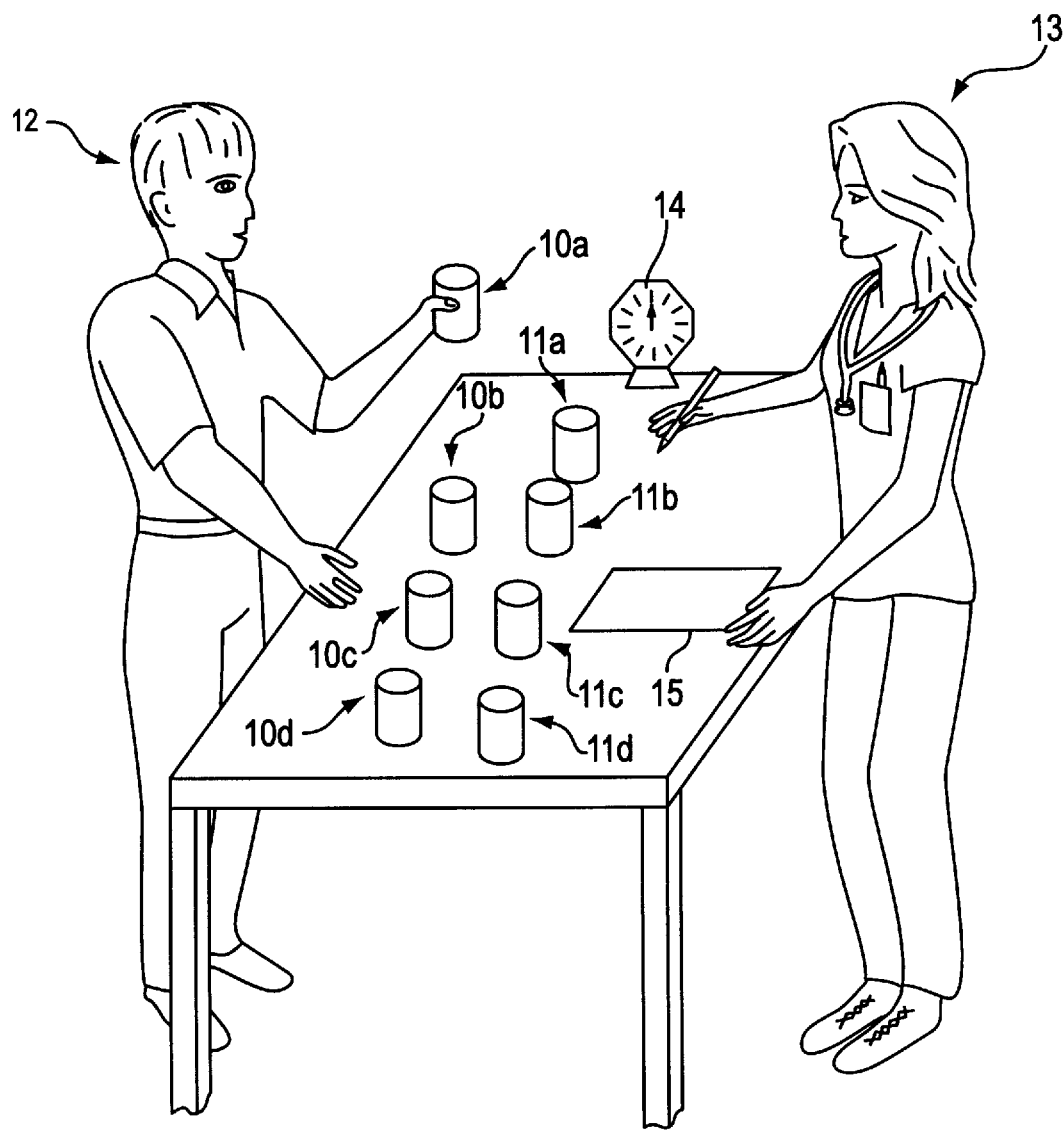

METHOD FOR TESTING FOR GASTROESOPHAGEAL REFLUX DISEASE

This application claims benefit of U.S. Provisional application Ser. No. 60/024,569, filed Aug. 26, 1996.

BACKGROUND OF THE INVENTION

1. Field of the Invention

This invention relates to medical diagnostic testing, and more particularly to a medical test that determines the likelihood that chest pain symptoms can be attributed to the reflux of acidic gastric contents.

2. Description of the Prior Art

Gastroesophageal reflux is a common human condition arising from the backwash or "reflux" of stomach acid into the esophagus. Mild reflux with "heartburn" is a very common condition experienced by nearly everyone at one time or another. However, prolonged or repeated bathing of the esophagus with gastric acid may lead to gastroesophageal reflux disease or "GERD." GERD is a disease that produces symptoms and/or tissue damage secondary to the reflux of gastric contents into the esophagus. A primary symptom of GERD is heartburn.

The prevalence of GERD in the U.S. population is increasing and, at a minimum, effects approximately ten percent (10%) of the U.S. population. This segment of the population has heartburn daily. More than one-third of the U.S. population, however, is estimated to have intermittent heartburn symptoms. Left untreated, GERD may lead to esophagitis, an esophageal ulceration, stricture or a malignant tumor formation.

Early diagnosis is an important aspect in the successful treatment and prevention of the progression of GERD. While many patients experience heartburn-like symptoms during reflux, it is difficult to quantify the degree or extent of the reflux from the symptoms alone. Moreover, since the symptoms of GERD often mimic cardiac chest pain, the physician must confirm that the symptoms are in fact due to reflux and not to a cardiac condition. The treatment of GERD largely involves the suppression or neutralization of acid. An appropriate treatment should, therefore, only be initiated in patients in whom it can be determined that the symptoms are related to esophageal mucosal contact arising from the retrograde flow of acid from the stomach into the esophagus.

The majority of individuals with reflux symptoms such as heartburn are never seen by physicians. A smaller yet significant group of individuals has persistent symptoms of reflux without complications and is more likely to occasionally seek medical attention. The majority of individuals with mild GERD manage their condition through the use of antacids, while a growing number are tuning to acid suppression medications, which are now sold without prescription, such as cimetidine (Tagamet®), famotidine (Pepcid®), or ranitidine (Zantac®). The treatment of suspected GERD using prescription acid suppression medication is relatively expensive and costs the U.S. health care system billions of dollars each year. Furthermore, it is estimated that Americans spend nearly one billion dollars each year on antacids alone. Many antacid users as well as patients who are taking prescription acid suppression drugs do so on the presumption that they have acid-related symptoms which could lead to or indicate GERD.

In terms of diagnosing GERD, one known method, that is fairly sensitive, uses endoscopy in order to permit direct visualization of the esophagus. This examination may reveal erosions, ulcerations, exudates, strictures or other complications associated with GERD. However, only patients with daily heartburn and other associated GERD symptoms would be likely candidates for endoscopy due to the costs and inconveniences associated with the procedure.

Other known tests involve the measurement of the acidity of the patient's esophagus over an extended period of time. Various devices for ambulatory pH testing are known, such as that shown in U.S. Pat. No. 4,503,859, issued to Petty et al., and U.S. Pat. No. 5,117,827, issued to Stuebe et al.

Another method of establishing a presumptive diagnosis of GERD is to measure the pressure in the lower esophagus. A relatively low pressure (less than 10 mmHg) between the esophagus and the stomach provides reasonable evidence that there is an incompetent barrier to reflux. A tool for making these pressure measurements is shown in U.S. Pat. No. 4,168,703, issued to Kenigsberg.

Another test for determining whether a symptom is secondary to reflux and, therefore may be associated with GERD, is known as the Bernstein acid perfusion test. With this test, saline is dripped through a catheter that has been inserted through the patient's nose to the middle of the esophagus. Without the patient's knowledge, a dilute 0.1N hydrochloric acid solution is substituted for the saline in the catheter to see if any symptoms are triggered. The acid solution is infused until the patient experiences symptoms or for approximately twenty (20) minutes if no symptoms occur. Saline is then reintroduced into the catheter to wash out the hydrochloric acid. The catheter is used primarily because the taste of the acid solution would alert the patient to the presence of the acid. A positive result (reproduction of typical chest pain symptoms) indicates acid sensitivity in the esophageal lining. Such a positive result will typically occur in about 80% of patients with reflux. Because of the necessity of nasogastric intubation, which is uncomfortable for the patient, and the fact that this procedure must be done in a physician's office, a simpler diagnostic tool is needed.

Currently, there is no simple diagnostic test or procedure that can be done either in a physician's office or in an individual's home to assist with the diagnosis of acid reflux and GERD.

SUMMARY OF THE INVENTION

The present invention provides a simple and effective procedure for determining the presence of esophageal acid sensitivity (EAS) and, in particular, the presumptive link between a patient's symptoms and esophageal acid contact (EAC) or acid reflux which may be an indication of GERD. The test of the present invention particularly provides an accurate indication of the relationship between the presence of acid in the patient's esophagus and symptoms the patient may be experiencing. Using the test of the present invention, an initial screening can be performed without the necessity of endoscopy and without the need for the insertion of a catheter into the esophagus as is required for the standard Bernstein test.

The test of the present invention also determines the absence of acid-related esophageal symptoms in a patient with a high degree of accuracy. Thus, by using the easily administered test of the present invention, it can be determined whether the patient is a likely candidate for further evaluation or for treatment using an acid suppressing medication. Or, by ruling out the presence of acid-related symptoms, the administration of potentially expensive testing or treatments which would be unnecessary and ineffective can be eliminated.

In accordance with the present invention, an acid solution, which has a similar hydrogen ion concentration or pH to the acid solution used in the Bernstein test, is swallowed by the patient rather than introduced through a catheter. The acid solution, however, has been modified so that the taste is palatable to the patient. To provide a control, the patient also swallows a dose of a neutral solution. The taste of the neutral solution is masked with a flavoring so that the taste more closely resembles the taste of the acid solution. The patient, therefore, will not know whether he or she is consuming the acid solution or the neutral solution.

The test includes simple steps that permit the procedure to be performed by a medical assistant in a physician's office or a pharmacy, or even to be self-administered by the patient at home. The steps comprise having the patient drink a controlled quantity of a neutral solution having a pH of approximately greater than 4.0 followed by an acid solution having a pH of approximately 3.0 or less. The reaction of the patient to each solution is noted. A positive test occurs if the patient responds with typical chest pain symptoms with the acid solution infusion and not with the neutral solution. A negative test occurs when the patient reports similar responses to both solutions.

The procedure thus provides a quick, easy, and inexpensive way to determine whether a patient may have acid-related symptoms, that could lead to or indicate GERD, and, therefore, may be a candidate for more extensive screening or treatment. A positive finding would allow the physician to initiate treatment with confidence that the appropriate abnormality is being treated. A negative finding may alert the physician to other causes to the patient's symptoms, such as cardiac disease, esophageal dysmotility, or even psychological causes.

The present invention thus provides a diagnostic solution which provides a quick and easy way for a health care professional to determine the management pathway for an individual who may be complaining of symptoms associated with EAC which in some instances may mimic angina, the primary symptom of coronary artery disease.

BRIEF DESCRIPTION OF THE DRAWINGS

The above and other objects and advantages of the invention will become apparent from consideration of the following detailed description when read in conjunction with the accompanying FIGURE in which like reference characters refer to like parts throughout, and in which:

The FIGURE is perspective view illustrating the apparatus used to conduct a test to determine the presence of esophageal acid sensitivity in a patient in accordance with the present invention.

DETAILED DESCRIPTION OF THE PREFERRED EMBODIMENTS

The present invention involves the oral administration to a patient of two liquid solutions, one acidic and the other neutral. In accordance with the present invention, the patient swallows controlled quantities of each solution, and the patient is monitored for any resulting symptoms.

The acid solution preferably is a dilute solution with a hydrogen ion concentration or pH of 3.0 or less. Ideally, the acid solution would have a pH approximating that of the 0.1N hydrochloric acid (HCl) used in the Bernstein test (i.e., a pH of approximately 1.2) and would be sufficiently palatable for oral consumption by a patient. Various acidic solutions were tested in order to find appropriate solutions. Numerous combinations of commercially available juices were tested such as concentrated lemon juice and fruit juices such as grape juice, grapefruit juice, and orange juice. None of these juices, however, had a sufficiently low pH so that the juice could be utilized alone. Various amounts of 0.1N hydrochloric acid were added to the juice solutions to see if some combination would result in a solution having a sufficiently low pH and adequate palatability. A difficulty arose, however, in adding enough acid to the solution to get the pH below 2.0 (considered the ideal pH for the purposes of this test) and still making the solution tolerable for oral consumption.

An acceptable solution that was both palatable and had a low enough pH was found by combining citric acid and the artificial sweetener, sorbitol. In one preferred embodiment of the invention, a suitable acid solution is obtained by mixing six parts citric acid solution with one part sorbitol solution in order to obtain a pH of approximately 1.8. For example, 60 milliliters (60 ml) of citric acid solution may be combined with 10 ml of sorbitol solution. The citric acid solution may be obtained by mixing approximately twenty-one grams (21 g) of anhydrous citric acid per one milliliter (1 ml) of water or normal saline solution. Normal saline solution is 0.9% sodium chloride i.e., each one hundred milliliters (100 ml) contains nine-hundred milligrams (900 mg) of sodium chloride in water. In the preferred embodiment of the invention, the sorbitol solution may be a 70% sorbitol solution, i.e., each 100 ml contains 700 g of powdered sorbitol in water.

The neutral solution serves as a control solution and preferably has a pH of greater than 4.0. In the preferred embodiment of the invention, the neutral solution comprises approximately 140 ml of water and 20 ml of lemon juice. The patient drinks the neutral solution which is flavored with the sour taste of the lemon juice in order to simulate the taste of but not the reaction to the acid solution. The lemon juice may be lemon extract, fresh lemon juice, concentrated or from concentrate, and the amount added may be modified to adjust the taste. However, the amount of lemon juice should not be so great as to lower the pH of the solution below 4.0.

With reference to FIG 1, the following describes a preferred embodiment of the administration of the test in accordance with the present invention:

1. A quantity of the palatable acid solution having a pH of 3.0 or less and of the neutral or control solution having a pH greater than 4.0 is prepared. The neutral solution is placed in four cups 10*a* through 10*d* illustrated in the FIGURE. The control solution is placed in four cups 11*a* through 11*d*;

2. Next the patient 12 ingests a dose of the neutral solution. In particular, a small swallowing cup 10*a* (approximately 50 ml) is filled with the neutral solution and then swallowed by the subject 12. Approximately one minute later as observed by an attendant 13 monitoring a timer 14, another cup of neutral solution 10*b* is ingested, and this is repeated until four cups 10*a* through 10*d* of neutral solution are ingested;

3. After each cup is ingested, the attendant 13 waits approximately 30 to 40 seconds, observing the timer 14, and asks the patient 12 if he or she is experiencing any symptoms, and if so, are the symptoms similar to the typical "heartburn" that the patient 12 has had in the past. The patient's 12 response is noted on a standard form 15. The form 15 preferably provides spaces for entry of the amount and timing of the doses and the patient's 12 response after each dose. An example of an acceptable form is shown in Appendix A herein.

4. After ingesting four cups 10a through 10d of approximately 50 ml each of the neutral solution, the subject then ingests four cups 11a through 11d of approximately 50 ml each of the acid solution in a similar manner. Following the same protocol as with the neutral solution, the subject 12 is queried by the attendant 13 approximately 30 to 40 seconds after ingesting each acid solution as to the presence of typical symptoms of heartburn.

Preferably, the doses of the solutions are coded to distinguish them from each other so as to be capable of identification. For example, the cups of acid solution 11a through 11d may be marked with a number, e.g., "1", and the cups of neutral solution may be marked with a different number, e.g., "2". Or, the cups holding the doses of solution may be marked with different colors. The administrator 13 of the test would hold the key to the coding in order to ensure that the patient's responses to the various doses are attributed to the correct solution (i.e., to the neutral or acid solution).

A positive test result occurs if no typical heartburn symptoms occur with the ingestion of the neutral solution, but the patient's typical, or recognizable heartburn symptoms are reproduced with the acid solution. A negative test result occurs when the patient has no response to the acid solution or has similar responses to both the neutral and the acid solutions.

The test of the present invention can be very revealing in terms of making an appropriate initial diagnosis and decision with regard to patient management. First, an individual who has no response to the neutral solution, and clearly has some reproduction of typical heartburn with the acid solution is an individual who would very likely respond well to acid suppression therapy. In the judgement of the physician, this could be done by recommending over-the-counter (OTC) acid-suppressing drugs, or by giving the patient a prescription for a more potent acid-suppressing regimen. The vast majority of patients in this category will respond favorably to this form of treatment.

On the other hand, individuals who do not have any response to the acid solution, or individuals who have a similar response to both the neutral solution and the acid solution, are individuals who clearly do not have a specific esophageal acid sensitivity. These individuals should not be treated initially with an acid-suppressing drug, because there has been no proof that the patient has an acid-sensitive disease. This would eliminate from acid-suppressing treatment a substantial proportion of individuals who come to a physician's office with vague complaints of heartburn or acid indigestion whose symptoms are not related to acid regurgitation or reflux.

Taking this rationale one step further, individuals who complain of some type of vague chest pain, perhaps resembling angina, but not necessarily resembling heartburn, can also be similarly diagnosed with regard to whether their pain is related to an acid-sensitive esophagus or not. Again, this is very helpful in making a differential diagnosis in patients entering an emergency room or a physician's office with complaints of chest pain. Obviously, the initial focus of any work-up with a patient complaining of acute chest pain is to eliminate a cardiac source for the pain, but if this is ruled out initially, the evaluation should focus on esophageal acid sensitivity as a possible source of the pain.

In order to accurately determine if acid sensitivity is present, the acid solution should preferably have a pH of less than or equal to 2.0 or at least less than or equal to 3.0. An acid solution having a pH=1.8 has been determined to be suitable for the purposes of the present invention. As described above, a pH of 1.8 may be obtained by combining 60 ml of citric acid and 10 ml of sorbitol. The specific proportions of citric acid solution and sorbitol may be adjusted to obtain a higher or lower pH within the range mentioned above (i.e., less than or equal to 3.0); however, a sufficient amount of sorbitol should be added to preferably make the overall acid solution palatable.

Citric acid or other similar acids can be used in combination with sorbitol, both of which are readily attainable. For example, 0.1 normal hydrochloric acid (HCl) may be substituted for the citric acid; however, as mentioned above, the resulting solution may not be as palatable. In any case, the acid should be suitably diluted so that it can be safely swallowed. Since the acid solution, even when diluted with water and sorbitol can have a sour taste, the taste of the acid solution may also be further masked by suitable flavorings such as vanilla, etc. Preferably, the amount of the flavoring is kept to a minimum so that the pH of the acid solution is not significantly affected.

Other sweeteners or flavorings may also be substituted for or used with the sorbitol in the acid solution. In another embodiment of the invention, approximately 60 ml of sweetened corn syrup may be mixed with 60 ml of a citric acid solution (21 grams of citric acid to 1000 ml of water) to obtain a pH of approximately 1.8. A suitable sweetened corn syrup is light corn syrup sold under the trademark KARO®, which contains light corn syrup with high fructose corn syrup, salt and vanilla. The syrup increases the viscosity of acid solution resulting in longer contact being made with the patient's esophagus. Other sweeteners may include natural-occuring sugars, such as sucrose, fructose, and other types of sweetened corn syrup, and sugar substitutes such as aspartame (sold under the trade name NutraSweet).

The neutral or control solution preferably has a pH higher than approximately 4.0. Preferably, the sour taste of the acid solution is mimicked by also providing the neutral solution with a sour taste. The lemon juice in the preferred embodiment of the neutral solution provides the sour taste. The lemon flavor and its accompanying sourness, gives the patient the impression that the neutral solution is also acidic and reduces the likelihood of invalid test results occurring do to the patient's anticipation of a desired affect. Whereas lemon juice is preferable due to its tartness, lime juice may also be used. Furthermore, where additional, masking-type, flavoring is added to the acid solution (e.g., vanilla flavoring or more sweeteners), similar masking flavoring may be added to the neutral solution.

While the neutral and acid solutions may be swallowed in either order, it is preferred that the neutral or control solution be swallowed first. For patients with GERD, the swallowing of the acid solution will cause irritation of the esophagus, and the irritation may continue well after the patient has stopped drinking the acid solution and has begun drinking the neutral solution, producing false positives when the patient drinks the neutral solution. By drinking the neutral solution first, the likelihood of false positive results due to this induced irritation is eliminated.

In addition, the number of doses, size of doses, and the frequency of ingestion of the doses may be modified. For example, in another embodiment of the invention, six (6) doses of approximately 20 ml of the neutral solution may be ingested every two to three minutes followed by six (6) doses of approximately 20 ml of the acid solution every two to three minutes. In still another example, 35 ml of the solutions are ingested every five minutes (see Appendix A, for example). A greater frequency of the ingestion of the solutions provides a more continual bathing of the esophagus, however, thereby providing a better opportunity for heartburn-like symptoms to arise where the patient has a sensitivity to esophageal acid contact.

As can be appreciated, the simplicity of the oral test of the present invention allows it to be administered outside of a physician's office. The test can be easily performed in a clinic by a nurse or physician's assistant, by a pharmacist in a pharmacy, or even by the patient alone in the patient's home.

Test Examples

In order to validate the effectiveness of the invention, the test was administered to a number of volunteers, five of whom had previously been shown to have a positive Bernstein test and had symptoms of GERD. Each volunteer was first given intermittent oral doses of the acid solution obtained by mixing 60 ml of dilute citric acid with 10 ml of dilute sorbitol. Next the volunteer took intermittent doses of the neutral solution obtained by mixing 140 ml of water with 20 ml of concentrated lemon juice. The pH of the acid solution was approximately 1.8. The results of the oral test of the present invention and a comparison of these results with the Bernstein test results can be summarized in the following table:

|  | Bernstein Results |  | Oral Test Results |  |
| --- | --- | --- | --- | --- |
| Subject | Positive | Negative | Positive | Negative |
| A | Yes |  | Yes |  |
| B | Yes |  | Mildly |  |
| C | Yes |  | Yes |  |
| D | Yes |  | Mildly |  |
| E | Yes |  | Yes |  |
| F |  | Yes |  | Yes |
| G |  | Yes | Yes |  |
| H |  | Yes |  | Yes |
| I |  | Yes | Yes |  |

With respect to those patients having positive Bernstein test results, Patient B experienced mild heartburn symptoms while drinking the acid solution and also experienced some heartburn symptoms while drinking the neutral solution, but these latter symptoms were attributed to the residual irritation of the esophagus induced while drinking the acid solution. Similarly, Patient D experienced heartburn symptoms while drinking both solutions, but the heartburn symptoms experienced while drinking the acid solution were of greater intensity than those experienced while drinking the neutral solution. Patient E also experienced very weak heartburn symptoms while drinking the neutral solution, but these symptoms abated as additional doses of the neutral solution were administered.

With respect to the patients having negative Bernstein test results, Patient G is indicated as having a positive oral test result, but it should be noted that this patient experienced some heartburn symptoms while drinking both the acid solution and the neutral solution, although the symptoms were somewhat more severe while drinking the acid solution, so the testing results for this patient were not entirely conclusive. Patient I also experienced some heartburn symptoms while drinking both solutions, although the symptoms were more severe while drinking the acid solution. In both cases, there is a possibility that the patients may have been reacting to the perceived acidity of the solution being consumed rather than reacting to the acid sensitivity of the esophageal lining. The remaining patients experienced typical heartburn symptoms if Bernstein positive, or no symptoms if Bernstein negative when drinking the acid solution, and experienced no symptoms when drinking the neutral solution.

These test results demonstrate that the oral test of the present invention accurately matched the results of the Bernstein acid perfusion test in 7 out of 9 subjects, or 77% of the time. Furthermore, the test was 100% accurate in those subjects in which the Bernstein test also indicated acid reactivity meaning that, when the test erred, it erred toward false positives rather than false negatives. This means that the oral test of the present invention is highly accurate in providing initial screening for possible GERD so that further testing can be considered or treatment initiated.

To further determine the instances of false positives, a second group of tests was administered to ten normal volunteers without frequent heartburn. It should be noted that a small percentage of normal asymptomatic individuals will have a physiologically positive Bernstein test. The results of this test can be seen in the following table:

|  | Oral Test Results |  |
| --- | --- | --- |
| Subject | Positive | Negative |
| J |  | Yes |
| K | Mildly |  |
| L |  | Yes |
| M |  | Yes |
| N |  | Yes |
| O |  | Yes |
| P |  | Yes |
| Q |  | Yes |
| R |  | Yes |
| S | Yes |  |

With regard to these test results, Patients J–N received the neutral solution first, while Patients O–S received the acid solution first. Patient K's test results were mildly positive in that the patient reported to experiencing "very mild" heartburn while drinking the acid solution while reporting no symptoms when previously drinking the neutral solution. Patient Q experienced some burning sensation while drinking the acid solution but also reported a burning sensation when subsequently drinking the neutral solution. Patient S reported experiencing a "mild burning sensation" when drinking the acid solution and no symptoms when drinking the neutral solution. The remaining patients experienced no heartburn symptoms when drinking either solution.

As with the Bernstein test, this invention accurately confirmed that the vast majority of asymptomatic normal volunteers have negative results. Thus, if the test is negative, it is an effective tool for determining that symptoms are not acid-related, thus saving the need for further unnecessary acid-related testing and treatment of patients. Similarly, a positive test provides assurance that acid suppression treatment is appropriate and has high probability of success. It should also be noted that virtually every subject interviewed expressed the fact that the oral procedure was much more tolerable to them, and they greatly preferred to simply swallow the acid solution rather than have to undergo nasal intubation (as required by the Bernstein test). It was quite apparent that patient compliance with the oral procedure would be very high, and there would be very few instances where subjects would simply refuse a test based on the adversiveness of the procedure itself.

An example of an acceptable form for recording a patient's response to test of the present invention is shown in Appendix A. Space is provided for the administrator to check when each dosage has been administered and to indicate the patient's response to each dose. Furthermore, if heartburn-like symptoms are reported, the administrator can note whether the patient's symptoms were typical or atypical of the type of heartburn that the patient has suffered from in the past and whether the patient would then ordinarily take an antacid. The form includes portions for reporting responses to the citric acid/sorbitol solution and for the neutral solution. In addition, the code that is used to identify the doses may be noted on the form.

Other variations and modifications of the specific embodiments herein shown and described will be apparent to those skilled in the art, all within the intended spirit and scope of the invention. While the invention has been shown and described with respect to particular embodiments thereof, these are for the purpose of illustration rather than limitation. Accordingly, the patent is not to be limited in scope and effect to the specific embodiments herein shown and described nor in any other way that is inconsistent with the extent to which the progress in the art has been advanced by the invention.

Appendage A
(Sample Form For Recording Patient Response to Test)

Oral Test For Esophageal Acid Sensitivity
Code: __
Citric Acid/
Sorbitol Solution     No Sensation = 0   Sensation = 1   Unsure = 2

35 cc    __    Response: _____
5 min    __    Response: _____
70 cc    __    Response: _____
10 min   __    Response: _____
105 cc   __    Response: _____
10 min   __    Response: _____
140 cc   __    Response: _____
20 min   __    Response: _____

Typical __ Atypical __    Would take antacid? Yes __ No __

Code: __
Neutral Solution     No Sensation = 0   Sensation = 1   Unsure = 2

35 cc    __    Response: _____
5 min    __    Response: _____
70 cc    __    Response: _____
10 min   __    Response: _____
105 cc   __    Response: _____
10 min   __    Response: _____
140 cc   __    Response: _____
20 min   __    Response: _____

Typical __ Atypical __    Would take antacid? Yes __ No __

Sensation Relieved:  __ with neutral solution   __ during acid solution
                     __ after procedure          __ not relieved at all

What is claimed:

1. A method for determining the presence of esophageal acid sensitivity in a patient, comprising the steps of:
   having a patient swallow a controlled quantity of an acidic solution having a pH of 3.0 or less;
   recording any reactions of the patient to the drinking of said acidic solution;
   having the patient swallow a neutral solution;
   recording any reactions of the patient to the drinking of said neutral solution; and
   comparing the recorded reactions of the patient to the drinking of each of the solutions to determine if there is a presence of esophageal acid sensitivity in the patient.

2. A method for determining the presence of esophageal acid sensitivity, as recited in claim 1, wherein at least one of said acidic and neutral solutions is flavored to have a taste similar to the other solution.

3. A method for determining the presence of esophageal acid sensitivity, as recited in claim 1, wherein said neutral solution is flavored to have a taste similar to said acidic solution, said neutral solution being less acidic than said acidic solution.

4. A method for determining the presence of esophageal acid sensitivity, as recited in claim 1, wherein said acidic solution is flavored to have a taste that renders said acidic solution relatively palatable.

5. A method for determining the presence of esophageal acid sensitivity, as recited in claim 1, wherein the patient drinks said acidic and neutral solutions in several doses of approximately 50 milliliters or less each in order to bathe the esophagus in said acidic and neutral solutions.

6. A method for determining the presence of esophageal acid sensitivity, as recited in claim 1, wherein the patient drinks said acidic solution before drinking said neutral solution.

7. A method for determining the presence of esophageal acid sensitivity, as recited in claim 1, wherein the patient drinks said neutral solution before drinking said acidic solution.

8. A set of elements for use in conducting a test to determine the presence of esophageal acid sensitivity in a patient, comprising:
   a plurality of doses of a liquid acidic solution having a pH of 3.0 or less, each of said acidic solution doses having a controlled volumetric quantity of approximately 50 milliliters or less, said acidic solution doses being adapted to be swallowed by a patient;
   a plurality of doses of a liquid neutral solution having a pH above 4.0, each of said neutral solution doses having a controlled volumetric quantity of approximately 50 milliliters or less, said neutral solution doses being adapted to be swallowed by the patient; and
   recording medium on which any reactions of the patient to the drinking of the doses may be recorded;
   wherein said neutral solution doses and said acid solution doses are coded to distinguish them from each other and to be capable of being identified; and
   wherein at least one of the said acidic solution and said neutral solution is flavored to simulate the taste of the other solution.

9. The apparatus for conducting a test to determine the presence of esophageal acid sensitivity in a patient, as recited in claim 8, wherein said acidic solution comprises citric acid and a sweetener.

10. The apparatus for conducting a test to determine the presence of esophageal acid sensitivity in a patient, as recited in claim 8, wherein said neutral solution comprises water and a flavoring.

11. A method for determining the presence of esophageal acid sensitivity in a patient, comprising the following steps:

having the patient orally ingest a controlled quantity of an acid solution having a pH of approximately 3.0 or less and which is substantially palatable to the patient;

having the patient orally ingest a controlled quantity of a control solution having a pH approximately greater than 4.0 and approximating the taste of said acid solution;

recording any reactions of the patient to the ingestion of said acid solution;

recording any reactions of the patient to ingestion of said control solution; and comparing the recorded reactions of the patient to the ingestion of the acid solution with the recorded reaction of the patient to the ingestion of the control solution to determine if there is a presence of esophageal sensitivity in the patient.

12. The method of claim 11, wherein said acid solution comprises citric acid and a sweetener.

13. The method of claim 12, wherein said sweetener comprises sorbitol.

14. The method of claim 11, wherein said control solution comprises lemon juice and water.

15. The method of claim 11, wherein the patient ingests said controlled quantity of control solution before ingesting said controlled quantity of acid solution.

16. The method of claim 11, wherein the patient ingests said controlled quantity of acid solution before ingesting said controlled quantity of said control solution.

17. The method of claim 11, wherein said controlled quantity of acid solution comprises a plurality of small doses of said acid solution, each said small dose of said acid solution being orally ingested by the patient at intervals of a predetermined length of time, and wherein the reactions of the patient are recorded after each ingestion of said small dose of acid solution.

18. The method of claim 17, wherein said predetermined length of time is approximately between one and five minutes.

19. The method of claim 11, wherein said controlled quantity of control solution comprises a plurality of small doses of said control solution, each said small dose of said control solution being orally ingested by the patient at intervals of predetermined length of time, and wherein the reactions of the patient are recorded after each ingestion of said small dose of control solution.

20. The method of claim 19, wherein said predetermined length of time is approximately between one and five minutes.

21. A method for determining the presence of esophageal acid sensitivity in a patient, comprising the following steps:

having the patient orally ingest a controlled quantity of a palatable, acid solution comprising an acid and a flavoring;

having the patient orally ingest a controlled quantity of a control solution substantially similar in taste to said acid solution;

recording any reactions of the patient to the ingestion of said acid solution;

recording any reactions of the patient to the ingestion of said control solution; and comparing the recorded reactions of the patient to the ingestion of the acid solution with the recorded reactions of the patient to the ingestion of the control solution to determine if there is a presence of esophageal acid sensitivity in the patient;

wherein said control solution has an acidity that is less than the acidity of said acid solution.

22. The method of claim 21, wherein said acid of said acid solution comprises citric acid.

23. The method of claim 21, wherein said flavoring of said acid solution comprises a sweetener.

24. The method of claim 23, wherein said sweetener comprises sorbitol.

25. The method of claim 21, wherein said control solution comprises lemon juice.

26. The method of claim 21, wherein said acid solution has a pH of approximately less than or equal to 3.0 and said control solution has a pH approximately greater than 4.0.

* * * * *